US009540665B2

(12) United States Patent
Barbier et al.

(10) Patent No.: US 9,540,665 B2
(45) Date of Patent: Jan. 10, 2017

(54) PROCESS FOR PRODUCING ETHANOL FROM TEXTILE COTTON

(75) Inventors: Jacques Barbier, Montamise (FR); Frederic Bataille, Sevres-Anxaumont (FR); Alexandre Briand, Saint Cyr (FR)

(73) Assignee: VALAGRO CARBONE RENOUVELABLE POITOU-CHARENTES, Poitiers (FR)

( * ) Notice: Subject to any disclaimer, the term of this patent is extended or adjusted under 35 U.S.C. 154(b) by 550 days.

(21) Appl. No.: 13/133,073

(22) PCT Filed: Dec. 4, 2009

(86) PCT No.: PCT/FR2009/052417
§ 371 (c)(1),
(2), (4) Date: Jun. 6, 2011

(87) PCT Pub. No.: WO2010/063981
PCT Pub. Date: Jun. 10, 2010

(65) Prior Publication Data
US 2011/0236945 A1    Sep. 29, 2011

(30) Foreign Application Priority Data
Dec. 5, 2008    (FR) .................................... 08 58307

(51) Int. Cl.
C12P 7/10    (2006.01)
C12P 7/08    (2006.01)

(52) U.S. Cl.
CPC .. *C12P 7/10* (2013.01); *C12P 7/08* (2013.01); *Y02E 50/16* (2013.01)

(58) Field of Classification Search
None
See application file for complete search history.

(56) References Cited

U.S. PATENT DOCUMENTS

| | | | | |
|---|---|---|---|---|
| 4,237,226 A * | 12/1980 | Grethlein | ........................... | 435/99 |
| 4,246,221 A * | 1/1981 | McCorsley, III | .............. | 264/203 |
| 4,617,127 A * | 10/1986 | Light | ............................ | 210/651 |
| 4,642,287 A * | 2/1987 | Inoi et al. | ........................ | 435/99 |
| 4,790,905 A * | 12/1988 | Nivelleau de La Bruniere et al. | ................................ | 162/56 |
| 5,938,994 A * | 8/1999 | English | ..................... | B29B 9/06 264/102 |
| 5,975,439 A * | 11/1999 | Chieffalo et al. | ................ | 241/17 |
| 6,255,368 B1 * | 7/2001 | English | ..................... | B29B 9/06 524/13 |
| 8,168,038 B2 * | 5/2012 | Medoff | ........................... | 162/50 |
| 8,450,294 B2 * | 5/2013 | Lepilleur et al. | ................ | 514/54 |
| 8,518,683 B2 * | 8/2013 | Medoff et al. | ................. | 435/177 |
| 8,597,921 B2 * | 12/2013 | Medoff | ........................... | 435/165 |
| 8,603,787 B2 * | 12/2013 | Medoff | ........................... | 435/165 |
| 8,609,384 B2 * | 12/2013 | Medoff | ........................... | 435/165 |
| 8,945,352 B2 * | 2/2015 | Medoff | ..................... | C08H 8/00 162/192 |
| 2002/0018842 A1 * | 2/2002 | Dunlow | ......................... | 426/630 |
| 2007/0178569 A1 | 8/2007 | Leschine et al. | | |
| 2012/0214979 A1 * | 8/2012 | Heiskanen et al. | .............. | 536/56 |

FOREIGN PATENT DOCUMENTS

| | | |
|---|---|---|
| WO | 2007/071818 A1 | 6/2007 |
| WO | 2007/084711 A2 | 7/2007 |
| WO | 2007/091231 A1 | 8/2007 |

OTHER PUBLICATIONS

Sun et al. (Biores. Tech., vol. 83, 2002, pp. 1-11).*
Shen et al. (Bioprocess Bisyst. Eng., vol. 34, 2011, pp. 33-43).*
Barjenbruch et al. (Adv. in Eniron. Res., vol. 7, pp. 715-720, 2003).*
Aydin (Appl. Surface Sci., vol. 233, 2004, pp. 268-274).*
Lamsal et al. (Biomass & Bioenergy, vol. 34, pp. 1703-1710, 2010).*
Milne et al. (Industrial and Engin. Chem., vol. 31, No. 9, 1939, pp. 1076-1078.*
Morent et al. (Surface & Coatings Tech., vol. 202, 2008, pp. 3427-3449).*
Abdel-Halim et al. (Carbohydrate Polymers, vol. 74, 2008, pp. 707-711).*
Azam Jeihanipour et al.: "Ethanol production from cotton-based waste textiles", Bioresource Technology [Online], vol. 100, No. 2, Aug. 23, 2008, pp. 1007-1010, XP025535099, ISSN: 0960-8524, abstract; figure 1; table 1, p. 1008, col. 1, paragraph 1-p. 1009, col. 2, paragraph 4.
International Search Report, dated Sep. 2, 2009, from corresponding PCT application.

* cited by examiner

*Primary Examiner* — Hope Robinson
(74) *Attorney, Agent, or Firm* — Young & Thompson

(57) ABSTRACT

A recycled textile cotton used for producing ethanol by the execution of a process that includes a step of pretreatment of textile cotton by pulping in an extruder, which may or may not involve a grinding step prior to pulping in the extruder, a step of enzymatic hydrolysis, a step of filtration(s), and a step of fermentation.

16 Claims, No Drawings

PROCESS FOR PRODUCING ETHANOL FROM TEXTILE COTTON

This invention relates to the use of a particular raw material for producing ethanol.

The invention also covers a process for the production of ethanol from this biomass.

For several years, numerous studies have been conducted for replacing fossil energy sources by renewable energies. In particular, research has been oriented toward the creation of new fuels: agrofuels or ecofuels.

An ecofuel is a fuel that is produced from renewable organic materials of non-fossil origin. There are various techniques for production of ecofuels, in particular the production of oil and its derivatives, alcohol or gas fuels from plant or animal biomass. Currently, intense research is in progress on the transformation of plants into alcohol, in particular into ethanol.

However, the development of these fuels has significant drawbacks both in terms of yield and because they compete directly with food cultivation and ecosystems. In addition, the production capacity of raw materials is limited compared to the very significant quantities of fuels that are consumed.

It is therefore necessary to propose new methods for producing ethanol that is designed to be used as biofuel.

For this purpose, this invention proposes using a particular cellulose material: recycled textile cotton.

Cellulose is an essential element of the plant wall. It is the most abundant polymer on earth. Cellulose consists of a glucopyranose chain. It is known that its hydrolysis by cellulases leads to obtaining glucose molecules, simple sugars that can easily be fermented into ethanol by means of glycolysis.

The use of textile cotton for producing ethanol is known from the publication "Ethanol Production from Cotton-Based Waste Textiles" (JEIHANIPOUR AND TAHERZADEH MJ, BIORESOURCES TECHNOLOGY, Vol. 100, No. 2, published online on Aug. 23, 2008).

However, the process that is described, which provides in particular a chemical pretreatment stage, is not satisfactory in terms of yield and requires the use of concentrated products, which makes it not very economical and difficult to produce on the industrial scale.

This is why the objective of this invention is to eliminate the drawbacks of the prior art and to propose a new means for bioethanol production that is purely in terms of energy, that is more advantageous on the environmental plane, and that has better yields.

This invention has as its particular object a process for the production of ethanol from textile cotton that comprises the following stages:
 a) Pretreatment of textile cotton:
  Optionally grinding of textile cotton,
  Pretreatment of textile cotton that may or may not be ground by pulping in an extruder,
 b) Enzymatic hydrolysis,
 c) Filtration(s), preferably nominal filtration, ultrafiltration, and sterile filtration, and
 d) Fermentation.

Textile cotton or recycled textile cotton is defined as a collected raw material (clothing at the end of its service life, scraps of fabrics from the garment industry, dust, etc.) such as waste and is composed of more than 90% cellulose.

Advantageously, the recycled textile cotton makes it possible to increase the yields of ethanol production, compared to known lignocellulosic raw materials, because of its high cellulose content. The particular process that is an object of the invention makes it possible also to increase the yields. In addition, this process is very advantageous from the ecological and economic standpoint. It is simple to implement and easy to industrialize.

In a preferred manner, the process comprises a discoloration stage before the fermentation stage.

A process that is particularly suitable according to the invention comprises the following stages:
 a) Pretreatment of recycled textile cotton:
  Grinding of textile cotton,
  Pretreatment of ground textile cotton,
 b) Enzymatic hydrolysis,
 c) Ultrafiltration, nanofiltration, reverse osmosis, discoloration and/or sterile filtration,
 d) Fermentation, and
 e) Distillation and dehydration, preferably using a membrane by pervaporation.

This invention is now described in detail for each of the stages of the process.

Pretreatment stage a) has as its objective to make cellulose accessible for facilitating its enzymatic hydrolysis.

Actually, the cotton fiber, primarily composed of cellulose, has undergone different chemical treatments (mercerization, scraping, anti-shrinking treatment, anti-crushing treatment and dyes) for their primary application in the textile industry. The typical chemical composition of a cotton fiber is:
 Cellulose: 91.2%,
 Water: 7%,
 Wax: 0.5%,
 Nitrogen-containing materials: 0.7%,
 Articular substances: 0.3%, and
 Ashes: 0.3%.

The pretreatment of the raw material can be chemical and/or mechanical.

The chemical pretreatment consists in hydrolyzing the hemicelluloses. It may involve, for example, a hydrolysis in hot basic medium for solubilizing the hemicelluloses and a portion of lignin, or a hot weak acid medium for hydrolyzing hemicelluloses.

According to a preferred embodiment, the pretreatment of the raw material according to the invention is implemented by pulping the textile cotton in an extruder. The pulping makes it possible to separate the fibers and to increase the digestibility of the cellulose. Preferably, the textile cotton is pulped in an extruder at a temperature of between 60° C. and 180° C. and in the presence of a quantity of water that represents between 200% and 450% of the mass of said raw material. Advantageously, the pretreatment of the raw material by pulping in an extruder makes it possible to increase by a factor of 3 the yield of the enzymatic hydrolysis of cellulose. It also makes it possible to reduce the amount of enzyme used during stage b).

According to a particularly suitable embodiment, the pretreatment is preceded by a stage for grinding the recycled textile cotton that makes it possible to make the cellulose even more accessible for the purpose of its hydrolysis.

The stage for grinding the raw material can be executed by way of example using a cutting mill.

Stage b) consists in hydrolyzing cellulose using enzymes for obtaining a glucose-rich solution.

Hydrolysis can be executed using an enzymatic cocktail that consists of cellulases and β-glucosidase.

Preferably, hydrolysis is executed in a tank that is kept at a temperature of between 50° C. and 60° C. and at a pH of between 4 and 5.5 for at least 24 hours. The ratio of enzymes per gram of cellulose is between 0.5 and 2.5.

Stage c) consists in filtering the solution that is obtained after enzymatic hydrolysis of the cellulose.

According to a preferred variant of the invention, stage c) comprises the following stages:
Filtration to clarify the medium,
Ultrafiltration,
Reverse osmosis,
Discoloration, and/or
Sterile filtration.

After stage b), the reaction medium consists of a sugary juice, cellulases, non-cellulose compounds, and non-degraded cellulose.

A centrifuging stage prior to filtration makes it possible to eliminate the non-cellulose compounds and the non-degraded cellulose.

The ultrafiltration has as its objective to recycle and to reuse the enzymes that are used for hydrolysis.

This tangential ultrafiltration stage makes it possible to considerably reduce the production costs of ethanol, because the cost of the enzymes that are used for the hydrolysis of cellulose is very significant.

The ultrafiltration stage can be executed on a membrane such as a polysulfone membrane, with a cutoff threshold of 6 KDa, an inside diameter of the fiber of 0.8 mm, and an outside diameter of 1.4 mm. This membrane makes it possible to concentrate and to recover the enzymes (the concentrate), on the one hand, and the sugary juice (the permeate), on the other hand.

The recycled enzymes are then reused for treating another lot of cellulose biomass. They can be reused until two cycles without a significant loss of activity are achieved.

Reverse osmosis concentrates the permeate without evaporation. This stage makes possible a savings of energy relative to a conventional evaporation stage.

Discoloration makes it possible to keep the dyes of textile cotton in a resin. It can be done on a column using a resin that has an affinity with the aromatic cycles in such a way that the dyes of textile cotton remain in the column by affinity.

Sterile filtration prevents any contamination in the fermenter and ensures an optimal yield of the fermentation.

Fermentation stage d) has as its objective to ferment in ethanol the glucose that is contained in the filtered sugary juice by means of glycolysis using a yeast.

This stage is preferably preceded by a cooling of the reaction medium.

Fermentation can be done in a fermenter between 30° C. and 37° C., between 7 hours and 24 hours, and at a pH of between 3.8 and 5.0. Conventionally, the yeasts that are used can be *Saccharomyces cerevisiae*.

The yield of the fermentation reaches 0.4 g of ethanol per gram of glucose. The yeasts that are used for the fermentation can be recycled by microfiltration, with a cutoff threshold of 6 KDa, for being reused.

The fermentation stage is generally followed by a distillation/dehydration stage e) on a membrane that makes it possible to obtain an ethanol at 99.9%.

An example of a process that is particularly suitable according to the invention therefore comprises the following stages:
Grinding of recycled textile cotton (diameter of 4 to 6 mm),
Pretreatment of ground textile cotton by pulping in a twin-screw extruder at a temperature of between 60° C. and 180° C. and in the presence of a quantity of water that represents between 200% and 450% of the mass of said raw material,
Enzymatic hydrolysis using an enzymatic cocktail that consists of cellulases and β-glucosidase (between 0.1 and 1 g of enzyme per gram of cellulose) in a tank that is kept at a temperature of between 50° C. and 60° C., and at a pH of between 4 and 5.5 for at least 24 hours,
Filtration to clarify the medium,
Ultrafiltration for recycling the enzymes of the hydrolysis,
Reverse osmosis,
Discoloration,
Sterile filtration,
Cooling,
Fermentation in a fermenter between 30° C. and 37° C., between 7 hours and 24 hours, at a pH of between 3.8 and 4.5, with *Saccharomyces cerevisiae*,
Microfiltration for recycling yeasts, and
Distillation/dehydration.

Such a process thus resolves the initial problem that is posed of the production of significant yields of bioethanol, starting from a raw material that is advantageous on the environmental plane.

The results that are obtained after enzymatic hydrolysis based on pretreatment (comparison made on the same biomass):
Pretreatment of textile cotton according to the invention, pulping (105° C. with 300% water),
Pretreatment of textile cotton according to the prior art (baking with 1% hydrochloric acid at 170° C. for 15 minutes), and
Without pretreatment,
are presented in the table below:

| Treatment of the Biomass | Glucose Levels in g/L$^{-1}$ | Percentage of Hydrolysis of the Intermediate Product |
|---|---|---|
| None (Control) | 17 | 38 |
| Chemical Pretreatment | 20 | 45 |
| Pretreatment According to the Invention | 36 | 82 |

It is noted that compared to no pretreatment or to pretreatments of the prior art, the process according to the invention makes it possible to considerably increase the hydrolysis of the cellulose and therefore the yield in terms of ethanol production. By the same token, this process makes it possible to reduce the production costs by recycling the enzymes and the yeasts that are used.

The ethanol that is obtained can advantageously be used as fuel in a gasoline vehicle, alone or combined with one or more other fuels.

The invention claimed is:

1. A process for the production of ethanol from textile cotton, comprising the steps of:
   a) Pre-treating textile cotton, said pre-treating consisting of a mechanical process selected from the group consisting of:
      (1) pulping a mixture of textile cotton and water in a twin-screw extruder at a temperature of between 60° C. and 180° C., wherein the water represents between 200% and 450% of the mass of the textile cotton,
   and
      (2) (i) grinding textile cotton,
         (ii) pulping a mixture of the ground textile cotton obtained from (i) with water in a twin-screw extruder at a temperature of between 60° C. and 180° C., wherein the water represents between 200% and 450% of the mass of the ground textile cotton;
b) Performing enzymatic hydrolysis of the pre-treated textile cotton and water mixture to form a medium comprising a sugary juice, enzymes used in said enzymatic hydrolysis, non-cellulose compounds, non-degraded cellulose, and dye from the textile cotton;
c) Performing filtration of the medium to separate the sugary juice from the enzymes, non-cellulose compounds, non-degraded cellulose and dye;
d) Fermenting the sugary juice with yeast, and
e) Obtaining ethanol from step d).

2. The process for the production of ethanol from textile cotton of claim 1, further comprising a step of performing discoloration to remove the dye before step d).

3. The process for the production of ethanol from textile cotton of claim 1, wherein the filtration of step c) comprises:
(i) Filtration to clarify the medium by removing the non-cellulose compounds and the non-degraded cellulose from the medium;
(ii) Ultrafiltration of the clarified medium to concentrate and remove the enzymes and to obtain a permeate comprising the sugary juice and the dye;
(iii) Reverse Osmosis to concentrate the permeate;
(iv) Discoloration to remove dye from the permeate to obtain the sugary juice;
(v) Sterile filtration of the sugary juice; and
(vi) Cooling.

4. The process for the production of ethanol from textile cotton of claim 1, wherein the ethanol is obtained in step e) by distillation or dehydration.

5. The process for the production of ethanol from textile cotton of claim 4, wherein the distillation or dehydration is executed using a membrane by pervaporation.

6. The process for the production of ethanol from textile cotton of claim 2,
wherein the process further comprises a step of performing microfiltration for recycling the yeasts used in step d);
wherein the ethanol is obtained in step e) by distillation or dehydration;
wherein the enzymatic hydrolysis in step b) comprises using an enzymatic cocktail that consists of cellulases and β-glucosidase;
wherein the filtration of step c) comprises performing:
(i) Filtration to clarify the medium by removing the non-cellulose compounds and the non-degraded cellulose from the medium,
(ii) Ultrafiltration of the clarified medium to concentrate and to remove the cellulases and β-glucosidase for recycling and to obtain a permeate comprising the sugary juice and the dye,
(iii) Reverse osmosis for concentrating the permeate,
(iv) Discoloration to remove the dye from the permeate to obtain a sugary juice,
(v) Sterile filtration of the sugary juice, and
(vi) Cooling; and
wherein step d) is performed in a fermenter between 30° C. and 37° C., between 7 hours and 24 hours, at a pH of between 3.8 and 5.0, with *Saccharomyces cerevisiae* as the yeast.

7. The process for the production of ethanol from textile cotton of claim 2, wherein the ethanol is obtained in step e) by distillation or dehydration.

8. The process for the production of ethanol from textile cotton of claim 3, wherein the ethanol is obtained in step e) by distillation or dehydration.

9. The process for the production of ethanol from textile cotton of claim 3,
wherein the process further comprises a step of performing microfiltration for recycling the yeasts used in step d);
wherein the ethanol is obtained in step e) by distillation or dehydration;
wherein the enzymatic hydrolysis in step b) comprises using an enzymatic cocktail that consists of cellulases and β-glucosidase; and
wherein step d) is performed in a fermenter between 30° C. and 37° C., between 7 hours and 24 hours, at a pH of between 3.8 and 5.0, with *Saccharomyces cerevisiae* as the yeast.

10. The process for the production of ethanol from textile cotton of claim 4
wherein the process further comprises a step of performing microfiltration for recycling the yeasts used in step d);
wherein the enzymatic hydrolysis in step b) comprises using an enzymatic cocktail that consists of cellulases and β-glucosidase;
wherein the filtration of step c) comprises performing:
(i) Filtration to clarify the medium by removing the non-cellulose compounds and the non-degraded cellulose from the medium,
(ii) Ultrafiltration of the clarified medium to concentrate and to remove the cellulases and β-glucosidase for recycling and to obtain a permeate comprising the sugary juice and the dye,
(iii) Reverse osmosis for concentrating the permeate,
(iv) Discoloration to remove the dye from the permeate to obtain a sugary juice,
(v) Sterile filtration of the sugary juice, and
(vi) Cooling;
wherein step d) is performed in a fermenter between 30° C. and 37° C., between 7 hours and 24 hours, at a pH of between 3.8 and 5.0, with *Saccharomyces cerevisiae* as the yeast.

11. The process for the production of ethanol from textile cotton of claim 1, wherein the pretreating consists of the mechanical process of:
(i) grinding textile cotton, and
(ii) pulping a mixture of the ground textile cotton obtained from (i) and water in a twin-screw extruder at a temperature of between 60° C. and 180° C., wherein the water represents between 200% and 450% of the mass of the ground textile cotton.

12. A process for the production of ethanol from textile cotton, comprising the steps of:
pretreating textile cotton, said pretreating consisting of a mechanical process of:
(i) grinding textile cotton to form a ground textile cotton and
(ii) pulping the ground textile cotton obtained in (i) with water that is between 200% and 450% of the mass of ground textile cotton in a twin-screw extruder at a temperature of between 60° C. and 180° C.;
preparing a reaction medium for enzymatic hydrolysis in which the pre-treated textile cotton and the water are combined with enzymes for hydrolysis;

filtering the medium after enzymatic hydrolysis to remove non-cellulose and non-degraded cellulose from the medium thereby obtaining a clarified medium;

subjecting the clarified medium to ultrafiltration to recover a concentrate and a permeate, the concentrate being enzymes of the hydrolysis and the permeate being a sugary juice;

subjecting the sugary juice to reverse osmosis to concentrate the sugary juice;

subjecting the concentrated sugary juice to sterile filtration to obtain a sterile concentrated sugary juice;

subjecting the sterile concentrated sugary juice to fermentation with yeast in a fermenter, recovering the yeast used in the fermenting by microfiltration; and distilling or dehydrating the fermented sugary juice to produce ethanol, wherein at least one of the recovered concentrate of enzymes or the recovered yeast is recycled in the enzymatic hydrolysis step or the fermentation step, respectively.

13. The method according to claim 12, wherein the enzymes used in the enzymatic hydrolysis consist of cellulases and β-glucosidase.

14. The method according to claim 12, wherein the yeast is *Saccharomyces cerevisiae*, and fermentation is carried out between 30° C. and 37° C., between 7 hours and 24 hours, at a pH of between 3.8 and 5.0.

15. The method according to claim 12, wherein the sterile concentrated sugary juice is cooled prior to fermentation.

16. The method according to claim 12, wherein discoloration is performed prior to fermentation to remove dye originating from the textile cotton.

* * * * *